(12) United States Patent
Wang et al.

(10) Patent No.: US 11,210,292 B2
(45) Date of Patent: Dec. 28, 2021

(54) SEARCH METHOD AND APPARATUS (71) Applicant: HUAWEI TECHNOLOGIES CO., LTD., Guangdong (CN)

(72) Inventors: Yasheng Wang, Shenzhen (CN); Yang Zhang, Shenzhen (CN); Hongbo Zhang, Shenzhen (CN)

(73) Assignee: HUAWEI TECHNOLOGIES CO., LTD., Guangdong (CN)

( * ) Notice: Subject to any disclaimer, the term of this patent is extended or adjusted under 35 U.S.C. 154(b) by 271 days.

(21) Appl. No.: 16/396,381

(22) Filed: Apr. 26, 2019

(65) Prior Publication Data
US 2019/0251084 A1  Aug. 15, 2019

Related U.S. Application Data (63) Continuation of application No. PCT/CN2016/103593, filed on Oct. 27, 2016.

(51) Int. Cl.
*G06F 16/00* (2019.01)
*G06F 16/2455* (2019.01)
*G16H 10/60* (2018.01)

(52) U.S. Cl.
CPC .......... *G06F 16/2455* (2019.01); *G06F 16/00* (2019.01); *G16H 10/60* (2018.01)

(58) Field of Classification Search
CPC ........ G06F 17/30864; G06F 17/30867; G06F 17/30286; G06F 17/30595; G06F 16/2455;
(Continued)

(56) References Cited

U.S. PATENT DOCUMENTS

| 2002/0078044 | A1  | 6/2002 | Song et al. | |
|---|---|---|---|---|
| 2014/0280353 | A1* | 9/2014 | Delaney | G06F 16/367 707/794 |
| 2017/0195240 | A1* | 7/2017 | Chen | H04L 45/70 |

FOREIGN PATENT DOCUMENTS

| CN | 102937960 A | 2/2013 |
|---|---|---|
| CN | 103678356 A | 3/2014 |

(Continued)

OTHER PUBLICATIONS

Yang Jin-Feng et al. An Overview of Research on Electronic Medical Record Oriented Named Entity Recognition and Entity Relation Extraction, ACTA Automatica Sinica, vol. 40, No. 8, Aug. 2014, total 26 pages. With English abstract.

(Continued)

*Primary Examiner* — Ashish Thomas
*Assistant Examiner* — Suman Rajaputra
(74) *Attorney, Agent, or Firm* — Womble Bond Dickinson (US) LLP (57) ABSTRACT

Embodiments of the present invention relate to the field of computer technologies, and provide a search method and apparatus to resolve a problem that a reference text, of a text in a professional field, that is determined by using the prior art has relatively low accuracy. The method includes: obtaining n named entities in a current to-be-analyzed target case (S300); determining a first characteristic and a second characteristic (S301); generating, based on the first characteristic and the second characteristic and according to a preset vector generation rule, a target characteristic vector corresponding to the target case (S302); obtaining each historical case in a database and a characteristic vector corresponding to each historical case (S303); and separately calculating a similarity between the target characteristic vector and the characteristic vector corresponding to each (Continued)

historical case, and selecting a historical case whose similarity result meets a preset condition as a reference case (S304).

12 Claims, 4 Drawing Sheets

(58) Field of Classification Search
CPC .... G06F 16/00; G06F 16/3334; G06F 16/335; G06Q 30/02; G16H 10/60; G16H 50/70
See application file for complete search history.

(56) References Cited

FOREIGN PATENT DOCUMENTS

| | | | |
|---|---|---|---|
| CN | 104679492 | A | 6/2015 |
| CN | 105260598 | A | 1/2016 |
| CN | 105389470 | A | 3/2016 |
| CN | 105677873 | A | 6/2016 |
| CN | 105930358 | A | 9/2016 |

OTHER PUBLICATIONS

Xia Han:"Research of Medical Named Entity Recognition Technology Based on Ontology", Shanghai Jiaotong University, Computer Software and Theory, 2012, Master, with English abstract. Total 83 pages.

\* cited by examiner

SEARCH METHOD AND APPARATUS

CROSS-REFERENCE TO RELATED APPLICATIONS

This application is a continuation of International Application No. PCT/CN2016/103593, filed on Oct. 27, 2016, the disclosure of which is hereby incorporated by reference in its entirety.

TECHNICAL FIELD

Embodiments of the present invention relate to the field of computer technologies, and in particular, to a search method and apparatus.

BACKGROUND

With advancement of information technologies, a growing quantity of cases are recorded, tracked, and stored at different electrical and automatic levels. Fast search for a reference case in massive cases plays an important role. Most cases are in a form of text, and therefore a search for a reference case may be understood as a search for a reference text.

Currently, there are two methods for searching for a reference text: (1) extracting a keyword of a target text, and searching a text database for a reference text that matches the keyword of the target text; (2) extracting a text keyword based on an natural language processing (NLP) technology, generating a keyword vector based on a quantity of occurrences of the keyword, calculating a distance between keyword vectors of different texts to determine a similarity between different texts, and searching for the reference text based on the similarity between different texts.

In many professional fields (such as the medical field and the judicial field), texts (such as medical records, psychological research cases, and criminal case volumes) have field characteristics in the way of expression, and each text is an individualized variation and combination of professional field knowledge. A text in a professional field often cannot be reflected only by keywords. For example, it is recorded in a medical record that "No dizziness. The father has diabetes". Keywords of the medical case are "dizziness" and "diabetes", but "dizziness" and "diabetes" cannot reflect true information of such a case. Using the foregoing search method to obtain a reference text of a text in a professional field may cause relatively low accuracy of the determined reference text.

SUMMARY

The present invention provides a search method and apparatus to effectively resolve a problem that a reference text, of a text in a professional field, that is determined by using the prior art has relatively low accuracy.

To achieve the foregoing objective, the present invention uses the following technical solutions.

According to a first aspect, a search method is provided, including: first obtaining n named entities in a current to-be-analyzed target case, and determining a first characteristic and a second characteristic, where the named entity is an entity identified with a proprietary name in a field to which the target case belongs; the first characteristic is a status of a correspondence between each of the n (n is a positive integer) named entities and a to-be-analyzed user, where the status includes presence or absence; and the second characteristic is a corresponding function impact of a preset m ($m \leq C_n^2$) on a target named entity, where the function impact includes facilitation or suppression, and the target named entity belongs to the n named entities; then generating, based on the first characteristic and the second characteristic and according to a preset vector generation rule, a target characteristic vector corresponding to the target case; finally obtaining each historical case in a database and a characteristic vector corresponding to each historical case; and separately calculating a similarity between the target characteristic vector and the characteristic vector corresponding to each historical case, and selecting a historical case whose similarity result meets a preset condition as a reference case.

The first characteristic in an embodiment of the present invention is a status of a correspondence between each of the n named entities in the target case and a to-be-analyzed user, and the second characteristic is a corresponding function impact of a preset m, in the n named entities in the target case, on a target named entity. Therefore, the first characteristic and the second characteristic can accurately reflect related information of each named entity in the target case. Correspondingly, the target characteristic vector corresponding to the target case generated based on the first characteristic and the second characteristic can accurately represent key information of the target case. In this way, accuracy in determining a reference case can be improved by using the target characteristic vector corresponding to the target case to search for the reference case.

Optionally, in a possible implementation of this embodiment of the present invention, the generating, based on the first characteristic and the second characteristic and according to a preset vector generation rule, a target characteristic vector corresponding to the target case includes: determining, according to a preset numeralization manner, a numeric value corresponding to the first characteristic and a numeric value corresponding to the second characteristic; generating, according to the preset vector generation rule, the numeric value corresponding to the first characteristic, and the numeric value corresponding to the second characteristic, a characteristic vector corresponding to the target case; and performing dimension reduction processing on the characteristic vector corresponding to the target case to generate the target characteristic vector corresponding to the target case.

In actual application, a dimension of a characteristic vector corresponding to a target case is quite high, and therefore, dimension reduction processing is performed on the characteristic vector corresponding to the target case to obtain a target characteristic vector corresponding to the target case with a lower dimension. In this way, a reference case can be obtained efficiently.

Optionally, in another possible implementation of this embodiment of the present invention, the search method provided by this embodiment of the present invention is applicable to the medical field, and the target case is a current to-be-analyzed electronic medical record. Correspondingly, the obtaining n named entities in a current to-be-analyzed target case includes: obtaining the current to-be-analyzed electronic medical record; performing word segmentation and stop word deletion processing on the current to-be-analyzed electronic medical record to obtain a word set; and performing medical-field named-entity identification on a word in the word set to determine n named entities in the current to-be-analyzed electronic medical record.

Optionally, in another possible implementation of this embodiment of the present invention, the preset condition is that a historical case with a highest similarity with the target case is selected as the reference case, or a historical case whose similarity with the target case is greater than a preset threshold is selected as the reference case.

According to a second aspect, a search apparatus is provided, and the search apparatus includes an obtaining unit, a determining unit, a generation unit, and a case search unit.

Functions implemented by the unit modules provided by an embodiment of the present invention are as follows:

The obtaining unit is configured to obtain n named entities in a current to-be-analyzed target case, where the named entity is an entity identified with a proprietary name in a field to which the target case belongs. The determining unit is configured to determine a first characteristic and a second characteristic, where the first characteristic is a status of a correspondence between each of the n (n is a positive integer) named entities obtained by the obtaining unit and a to-be-analyzed user, and the status includes presence or absence; and the second characteristic is a corresponding function impact of a preset m ($m \leq C_n^2$) on a target named entity, the function impact includes facilitation or suppression, and the target named entity belongs to the n named entities. The generation unit is configured to generate, based on the first characteristic and the second characteristic determined by the determining unit and according to a preset vector generation rule, a target characteristic vector corresponding to the target case. The obtaining unit is further configured to obtain each historical case in a database and a characteristic vector corresponding to each historical case. The case search unit is configured to separately calculate a similarity between the target characteristic vector generated by the generation unit and the characteristic vector corresponding to each historical case obtained by the obtaining unit, and select a historical case whose similarity result meets a preset condition as a reference case.

Optionally, in a possible implementation of this embodiment of the present invention, the determining unit is further configured to determine, according to a preset numeralization manner, a numeric value corresponding to the first characteristic and a numeric value corresponding to the second characteristic; and the generation unit is configured to generate, according to the preset vector generation rule, the numeric value corresponding to the first characteristic, and the numeric value corresponding to the second characteristic, a characteristic vector corresponding to the target case, and is configured to perform dimension reduction processing on the characteristic vector corresponding to the target case to generate the target characteristic vector corresponding to the target case.

Optionally, in another possible implementation of this embodiment of the present invention, the search apparatus provided by this embodiment of the present invention is applicable to the medical field, and the target case is a current to-be-analyzed electronic medical record. The obtaining unit is configured to: obtain the current to-be-analyzed electronic medical record; perform word segmentation and stop word deletion processing on the current to-be-analyzed electronic medical record to obtain a word set; and perform medical-field named-entity identification on a word in the word set to determine n named entities in the current to-be-analyzed electronic medical record.

Optionally, in another possible implementation of this embodiment of the present invention, the preset condition is that a historical case with a highest similarity with the target case is selected as the reference case, or a historical case whose similarity with the target case is greater than a preset threshold is selected as the reference case.

According to a third aspect, a search apparatus is provided, where the search apparatus includes a memory, a processor, and a communications interface, where the memory, the processor, and the communications interface are connected by using a system bus; and the memory is configured to store a computer instruction, and the processor is configured to execute the computer instruction stored by the memory to enable the search apparatus to perform the search method in the first aspect and the various possible implementations thereof.

According to a fourth aspect, a computer readable storage medium is further provided, where the computer readable storage medium includes one or more program codes; and when a processor of a search apparatus is executing the program code, the search apparatus performs the search method described in the first aspect and the various possible implementations thereof.

In the embodiments of the present invention, names of the search apparatus do not constitute a limitation on devices or function modules. In actual implementation, these devices or function modules may appear in other names. All devices or function modules with functions similar to those in the present invention fall within the scope defined by the claims of the present invention and equivalent technologies of the present invention.

For detailed descriptions of the second aspect, the third aspect, the fourth aspect, and the various possible implementations thereof, refer to the detailed descriptions of the first aspect and the various possible implementations thereof. In addition, for beneficial effects of the second aspect, the third aspect, the fourth aspect, and the various possible implementations thereof, refer to analysis of the beneficial effects in the first aspect and the various possible implementations thereof. Details are not repeated herein.

These or other aspects of the embodiments of the present invention will be more concise and understandable from the following description.

BRIEF DESCRIPTION OF DRAWINGS

To describe the technical solutions in the embodiments of the present invention more clearly, the following briefly describes the accompanying drawings required for describing the embodiments. Apparently, the accompanying drawings in the following description show merely some embodiments of the present invention.

DESCRIPTION OF EMBODIMENTS

The following describes the technical solutions in the embodiments of the present invention in detail with reference to the accompanying drawings in the embodiments of the present invention. Apparently, the described embodiments are merely some but not all of the embodiments of the present invention.

In the specification, claims, and accompanying drawings of the present invention, the terms "first", "second", and so on are intended to distinguish between different objects but do not limit a particular order. In addition, the terms "include", "contain", and any other variants thereof, are intended to cover a non-exclusive inclusion. For example, a process, a method, a system, a product, or a device that includes a series of operations or units is not limited to the listed operations or units, but optionally further includes an unlisted operation or unit, or optionally further includes another inherent operation or unit of the process, the method, the product, or the device.

In the following description, specific details such as a particular system structure, an interface, and a technology are set forth in an illustrative but not a restrictive sense to make a thorough understanding of the present invention. However, a person skilled in the art should know that the present invention may be practiced in other embodiments without these specific details. In other cases, detailed descriptions of well-known mobile devices, circuits, and methods are omitted, so that the present invention is described without being obscured by unnecessary details.

In addition, in the embodiments of the present invention, the word "exemplary" or "for example" is used to represent giving an example, an illustration, or a description. Any embodiment or design scheme described as an "exemplary" or "for example" in the embodiments of the present invention should not be explained as being more preferred or having more advantages than another embodiment or design scheme. Use of the word "exemplary," "for example," or the like is intended to present a related concept in a specific manner.

With advancement of information technologies, a growing quantity of cases are recorded, tracked, and stored at different electrical and automatic levels. Fast search for a reference case in massive cases plays an important role. For example, in the medical health field, each electronic medical record is a specific case in the medical field. The electronic medical record is a record of a patient's diagnosis and treatment process and a carrier of doctors' experience, and contains a large amount of information about the doctors' experience and individual differences between patients. Reference medical records can be used for curative effect comparison, medical knowledge discovery, and auxiliary diagnosis decision-making Therefore, reference medical record search and matching plays an important role in application and research, making full use of clinical values of medical big data information resources.

Generally, cases are in a form of text, and therefore a search for a reference case may be understood as a search for a reference text. Currently, a reference text is searched for mainly by using keywords of the text. For example, a keyword of the text is extracted based on an NLP technology, a keyword vector is generated based on a quantity of occurrences of the keyword, a distance between keyword vectors of different texts is calculated to determine a similarity between different texts, and the reference text is searched for based on the similarity between different texts. However, if the foregoing method is used to search for a reference text of a text in a professional field (such as medical records, criminal case volumes, and psychological research cases), a problem that the determined reference text has relatively low accuracy occurs.

A text in a professional field has its own unique characteristics, including expertise in the field and a special language mode. A vector including keywords is not enough to represent key information of a case. The most important information of a case is individualized expertise of the case in a field. For example, in an electronic medical record, a medically named entity (that is, a named entity in the electronic medical record) has quite important characteristics related to a patient (for example, diabetes is family-inherited), and these characteristics and the medically named entity can accurately represent key information of the electronic medical record. However, these characteristics and the medically named entity cannot be represented by a semantic model such as keyword matching or a simple term frequency vector. This is because structured knowledge, such as modification of a medically named entity and a relationship between different medically named entities, cannot be represented by an existing term frequency vector or other types of word vectors.

In summary, semantic relationship processing is ignored to some extent in a traditional similar-text search method, and the method is only limited to literal matching with a text character. For a text in a professional field, an obtained reference text has relatively low accuracy.

For a problem that a determined reference text of a text in a professional field has relatively low accuracy in the prior art, the present invention provides a search method: determining a first characteristic and a second characteristic, where the first characteristic represents a status of a correspondence between each of n named entities in a target case and a to-be-analyzed user, and the second characteristic represents a corresponding function impact of a preset m ($m \leq C_n^2$, in the n (n is a positive integer) named entities in the target case, on a target named entity; generating, based on the first characteristic and the second characteristic, a target characteristic vector corresponding to a target case, so that the target characteristic vector is used to represent key information of the target case; and calculating a similarity by using the target characteristic vector, so as to determine a reference case of the target case. The target characteristic vector can accurately represent the key information of the target case. Therefore, accuracy in determining a reference case can be improved by using the search method provided by embodiments of the present invention.

In the embodiments of the present invention, a current to-be-analyzed case is referred to as a target case, and a recoded case is referred to as a historical case. The search method provided by the embodiments of the present invention is to obtain, from at least one historical case, a historical case matching the target case.

The search method provided by the embodiments of the present invention is applicable to a search apparatus. The search apparatus may be a server or a client device, and this is not limited in the embodiments of the present invention.

Figure 1:
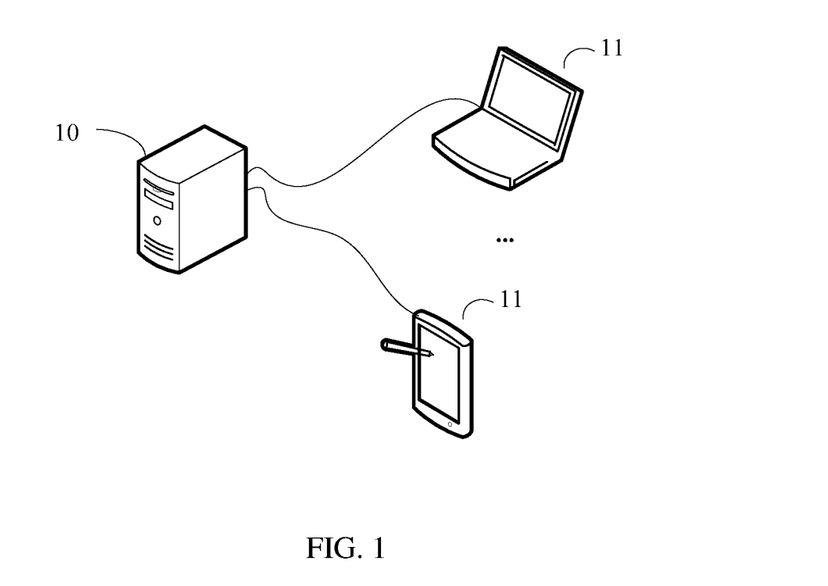
FIG. 1 is a schematic structural diagram of a network system according to an embodiment of the present invention.

Optionally, if the search apparatus is a server, the search method provided by the embodiments of the present invention is applicable to a network system. FIG. 1 is a schematic structural diagram of a network system according to an embodiment of the present invention. Referring to FIG. 1, the network system includes a server 10 and at least one client device 11, and the server 10 is connected to each client device 11 by using a network.

The server 10 is responsible for managing cases recorded by each client device 11, and has a function of searching for a reference case of a case for a client device and providing the reference case for the client device.

Figure 2:
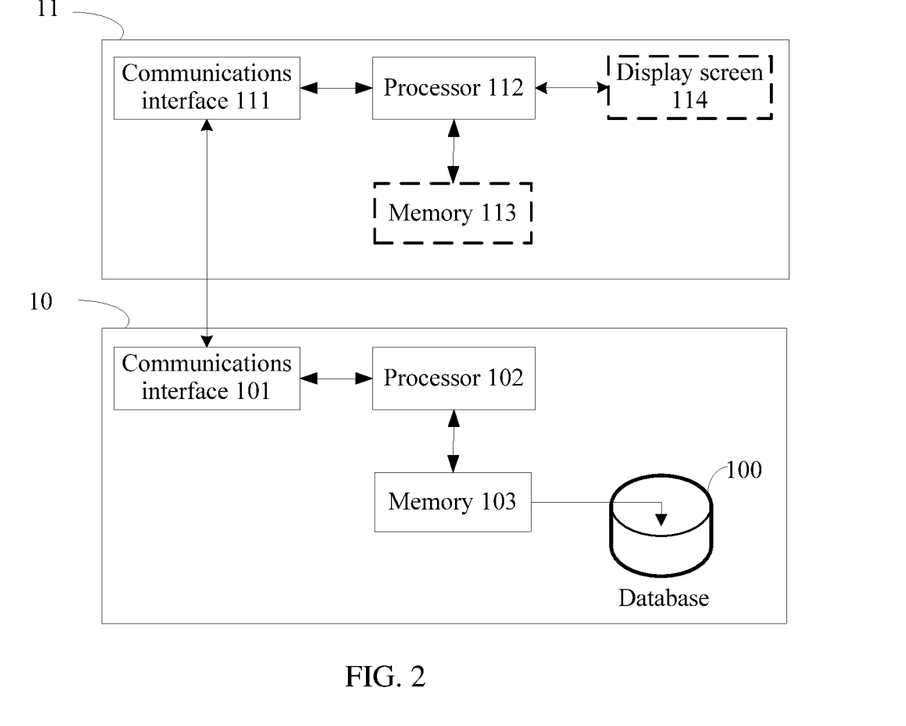
FIG. 2 is a schematic diagram of interaction and coordination between devices in a network system according to an embodiment of the present invention.

With reference to FIG. 1, FIG. 2 is a schematic diagram of interaction and coordination between the server 10 and the client device 11 in the network system. Processes of communication between each client device 11 and the server 10 in the network system are the same. For brevity, FIG. 2 shows communication between only one client device 11 and the server 10.

Referring to FIG. 2, the server 10 in the network system includes a database 100, where the database 100 stores a correspondence between a case characteristic and a case characteristic vector. The case characteristic includes a case identifier, and may further include specific text information of a case. The case identifier in the database 100 is used to indicate a historical case.

The server 10 further includes a communications interface 101, a processor 102, and a memory 103.

The communications interface 101 is configured to communicate with the client device 11 connected to the server 10. The memory 103 is configured to store the database 100, and may be further configured to store a software program and an application module. The processor 102 is configured to run or execute the software program and the application module stored in the memory 103, so as to execute various functions of the server 10.

The client device 11 in the network system includes a communications interface 111 and a processor 112. Optionally, the client device 11 may further include a memory 113 and a display screen 114. The memory 113 and the display screen 114 are optional, and therefore are represented by dashed lines in FIG. 2.

The communications interface 111 is configured to communicate with the server 10 connected to the client device 11. The memory 113 may be configured to store a software program and an application module. The processor 112 is configured to run or execute the software program and the application module stored in the memory 113, so as to execute various functions of the client device 11. The display screen 114 is configured to implement interaction between a user and the client device 11.

In addition, in this embodiment of the present invention, an application of the search apparatus serving as the client device is similar to an application of the search apparatus serving as the server. An only difference is that processing performed by the client device substitutes for communication between the server and the client device. The search apparatus serving as a client device is not described in detail herein again.

Figure 3:
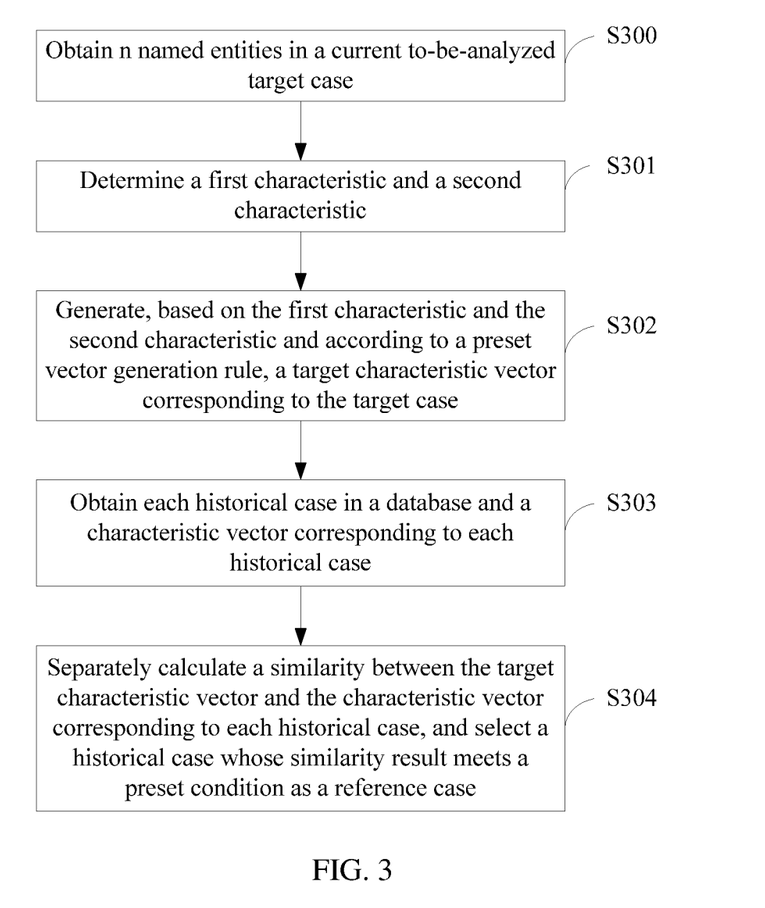
FIG. 3 is a schematic flowchart of a search method according to an embodiment of the present invention.

FIG. 3 is a schematic flowchart of a search method according to an embodiment of the present invention. The search method may be applied to the network system shown in FIG. 1 or FIG. 2.

Referring to FIG. 3, the search method includes the following operations.

S300. A search apparatus obtains n named entities in a current to-be-analyzed target case, where n≥1, and the named entity is an entity identified with a proprietary name in a field to which the target case belongs.

For example, if a field to which the target case belongs is the medical field, a named entity in the target case may be a disease name, a symptom name, an examination method, a treatment method, or the like.

S301. The search apparatus determines a first characteristic and a second characteristic.

The first characteristic is a status of a correspondence between each of the n named entities and a to-be-analyzed user, and the status includes presence or absence. The second characteristic is a corresponding function impact of a preset m on a target named entity, and the function impact includes facilitation or suppression. The target named entity belongs to the n named entities, and $m \leq C_n^2$.

S302. The search apparatus generates, based on the first characteristic and the second characteristic and according to a preset vector generation rule, a target characteristic vector corresponding to the target case.

S303. The search apparatus obtains each historical case in a database and a characteristic vector corresponding to each historical case.

S304. The search apparatus separately calculates a similarity between the target characteristic vector and the characteristic vector corresponding to each historical case, and selects a historical case whose similarity result meets a preset condition as a reference case.

The search apparatus in this embodiment of the present invention needs to first obtain the target case and determine the n named entities in the target case, in other words, the search apparatus performs S300.

After obtaining the target case, the search apparatus first performs preprocessing on the target case, such as word segmentation, stop word deletion, and punctuation removing, to obtain a word set. For example, there is a statement in an electronic medical record "Constipation occurred, accompanied by polyphagia, polydipsia, and polyuria symptoms, and without a fever or nausea symptom. High blood sugar was diagnosed in a local clinic, and a curative effect was poor after a Chinese patient hypoglycemic drug was given for oral administration. The mother suffered from diabetes". The search apparatus performs preprocessing on the sentences in the electronic medical record, such as word segmentation, stop word deletion, and punctuation removing to obtain a word set: occurred, constipation, accompanied, polyphagia, polydipsia, polyuria, symptom, without, fever, nausea, symptom, local, clinic, diagnose, high blood sugar, given, Chinese patient, hypoglycemic drug, oral administration, curative effect, poor, mother, suffer, and diabetes.

The search apparatus in this embodiment of the present invention may use any existing word segmentation processing algorithm, such as a conditional random field, a hidden Markov model, and a maximum entropy, and this is not limited in this embodiment of the present invention.

After obtaining the word set, the search apparatus performs named-entity identification on a word in the word set in a field to which the target case belongs.

For example, with reference to the previous example, after obtaining the word set "occurred, constipation, accompanied, polyphagia, polydipsia, polyuria, symptom, without, fever, nausea, symptom, local, clinic, diagnose, high blood sugar, given, Chinese patient, hypoglycemic drug, oral administration, curative effect, poor, mother, suffer, and diabetes" in the electronic medical record, the search apparatus identifies medially named entities in the word set. The medially named entities identified by the search apparatus are constipation, polyphagia, polydipsia, polyuria, fever, nausea, high blood sugar, diabetes, and hypoglycemic drug.

Further, after identifying the named entities in the word set, the search apparatus further determines an entity category of each named entity, where the entity category is determined based on specific expertise of a field.

For example, with reference to the previous example, in the named entities "constipation, polyphagia, polydipsia, polyuria, fever, nausea, high blood sugar, diabetes, and hypoglycemic drug", "constipation, polyphagia, polydipsia, polyuria, fever, nausea, and high blood sugar" are symptoms, "diabetes" is a disease, and "hypoglycemic drug" is a treatment method.

The method for identifying a named entity in the target case by the search apparatus in this embodiment of the present invention may be a dictionary-based method, a machine-learning-based method, or a method based on a combination of dictionary and machine learning. This is not limited in this embodiment of the present invention.

Further, after obtaining the n named entities in the target case, the search apparatus determines the first characteristic and the second characteristic, that is, S301 is performed.

After determining the n named entities of the target case, based on a definition of a status of a to-be-analyzed user and definitions of function impacts between different named entities in a field to which the target case belongs, the search apparatus determines a status of a correspondence between each of the n named entities and a to-be-analyzed user, and determines a corresponding function impact of a preset m on a target named entity in the n named entities, in other words, determines the first characteristic and the second characteristic.

For example, in the medical field, Table 1 shows definitions of statuses of a to-be-analyzed user corresponding to each medically named entity, and Table 2 shows definitions of function impacts between different medically named entities.

TABLE 1

| Status of a to-be-analyzed user | Definition |
|---|---|
| Yes | The patient is suffering from a disease, or a symptom is presented. |
| No | The patient denied a disease or a symptom, or no symptom is observed. |
| Possible | A possible disease diagnosis is made based on a current symptom. |
| Family-related | The disease or symptom is of a relative or a spouse of the patient. |

TABLE 2

| Function impact | Definition |
|---|---|
| Positive relationship | A treatment relieves the disease or symptom. |
| Negative relationship | A treatment deteriorates or results in the disease or symptom. |
| No relationship or no clear relationship | A treatment is not used or a result of a treatment used is unknown. |

With reference to the previous example, after the search apparatus obtains the named entities "constipation, polyphagia, polydipsia, polyuria, fever, nausea, high blood sugar, diabetes, and hypoglycemic drug", the first characteristic and the second characteristic determined according to Table 1 and Table 2 are as follows:

first characteristic: {constipation (yes), polydipsia (yes), polyphagia (yes), polyuria (yes), fever (no), nausea (no), high blood sugar (yes), diabetes (familial), hypoglycemic drug (yes)} second characteristic: {hypoglycemic drug-high blood sugar (negative relationship)}

The method for determining the first characteristic and the second characteristic by the search apparatus in this embodiment of the present invention may be a dictionary-based method, a machine-learning-based method, or a method based on a combination of dictionary and machine learning. This is not limited in this embodiment of the present invention.

Further, after determining the first characteristic and the second characteristic, the search apparatus generates, based on the first characteristic and the second characteristic and according to the preset vector generation rule, a target characteristic vector corresponding to the target case, that is, S302 is performed.

The search apparatus first determines, according to a preset numeralization manner, a numeric value corresponding to the first characteristic and a numeric value corresponding to the second characteristic, in other words, the search apparatus performs numeralization processing on the first characteristic and the second characteristic. Then, the search apparatus generates, according to the preset vector generation rule, the numeric value corresponding to the first characteristic, and the numeric value corresponding to the second characteristic, a characteristic vector corresponding to the target case.

The numeralization method used by the search apparatus to perform numeralization processing on the first characteristic and the second characteristic needs to be set based on knowledge characteristics of a field to which the target case belongs.

For example, as shown in Table 3, in the medical field, a status of a correspondence between each medically named entity and a to-be-analyzed user is numeralized based on an occurrence probability of the status; and function impacts between different medically named entities are numeralized based on positive and negative relationships of the function impacts.

TABLE 3

| Status of a to-be-analyzed user | | Function impact | |
|---|---|---|---|
| Yes | 1 | Positive relationship | 1 |
| No | 0 | Negative relationship | −1 |
| Possible | 0.5 | No relationship or no clear relationship | 0 |
| Familial | 0.25 | | |

With reference to the previous example, the search apparatus performs numeralization processing on the first characteristic and the second characteristic determined according to the numeralization manner shown in Table 3. A determined numeric value corresponding to the first characteristic and a determined numeric value corresponding to the second characteristic are as follows:

first characteristic: {constipation (1), polydipsia (1), polyphagia (1), polyuria (1), fever (0), nausea (0), high blood sugar (1), diabetes (0.25), hypoglycemic drug (1)} second characteristic: {hypoglycemic drug-high blood sugar (−1)}

After determining the numeric value corresponding to the first characteristic and the numeric value corresponding to the second characteristic, the search apparatus generates, according to the preset vector generation rule, the numeric value corresponding to the first characteristic, and the numeric value corresponding to the second characteristic, a characteristic vector corresponding to the target case.

For example, with reference to the previous example, the characteristic vector corresponding to the target case generated by the search apparatus is:

{constipation, polyphagia, polyphagia, polyuria, fever, nausea, high blood sugar, diabetes, hypoglycemic drug, hypoglycemic drug-high blood sugar}

{1, 1, 1, 1, 0, 0, 1, 0.25, 1, −1}

In actual application, the characteristic vector corresponding to the target case is usually an ultra-high-dimensional vector in tens of thousands of dimensions. To obtain a deep characteristic representation of the target case, dimension reduction processing is performed on the characteristic vector corresponding to the target case in this embodiment of the present invention, so that a low-dimensional target characteristic vector corresponding to the target case is obtained.

The search apparatus in this embodiment of the present invention performs, by using a pre-trained deep automatic encoder, dimension reduction processing on the characteristic vector corresponding to the target case.

To ensure that the target characteristic vector corresponding to the obtained target case is a deep characteristic representation of the target case, the deep automatic encoder in this embodiment of the present invention may perform dimension reduction processing on the characteristic vector corresponding to the target case in a way of combining an unsupervised manner and a supervised manner. At the first several layers of the encoder, the unsupervised manner is used, and at the last layer, a classifier with a supervision function is used to perform fine adjustment on encoder parameters.

For a method for training the deep automatic encoder by the search apparatus, refer to any existing method for training the deep automatic encoder. This is not limited in this embodiment of the present invention.

Further, the search apparatus obtains each historical case in a database and the characteristic vector corresponding to each historical case, separately calculates a similarity between the target characteristic vector and the characteristic vector corresponding to each historical case, and selects a historical case whose similarity result meets a preset condition as the reference case, that is, S303 and S304 are performed.

It can be learned from FIG. 2 that the search apparatus in this embodiment of the present invention includes a database. The database stores a correspondence between a characteristic of a case and a characteristic vector corresponding to the case, and cases in the database are historical cases.

For each historical case, the search apparatus in this embodiment of the present invention determines the characteristic vector corresponding to each historical case by using the method for determining the target characteristic vector corresponding to the target case, and then stores the characteristic vector corresponding to each historical case and the correspondence between the characteristic and the characteristic vector, so as to generate the database. It can be learned from the foregoing description that the characteristic vector corresponding to the target case can accurately reflect key information of the target case, and therefore, the characteristic vector corresponding to each historical case in the database can also accurately reflect key information of the historical case.

The characteristic vector corresponding to the target case can accurately reflect the key information of the target case, and the characteristic vector corresponding to the historical case can accurately reflect the key information of the historical case. Therefore, a similarity, separately calculated by the search apparatus based on the target characteristic vector and the characteristic vector corresponding to each historical case, between the target characteristic vector and the characteristic vector corresponding to each historical case is relatively accurate.

Optionally, for each historical case, the search apparatus calculates a distance between the characteristic vector corresponding to the target case and the characteristic vector corresponding to the historical case, and determines the distance as a similarity between the target case and the historical case.

After separately calculating the similarity between the target characteristic vector and the characteristic vector corresponding to each historical case, the search apparatus selects a historical case whose similarity result meets a preset condition as the reference case.

The preset condition is that a historical case with a highest similarity with the target case is selected as the reference case, or a historical case whose similarity with the target case is greater than a preset threshold is selected as the reference case.

After separately calculating the similarity between the target characteristic vector and the characteristic vector corresponding to each historical case, the search apparatus sorts the calculated similarities, and selects a historical case with a highest similarity with the target case as the case, or selects a historical case whose similarity with the target case is greater than the preset threshold as the reference case.

Generally, a quantity of historical cases whose similarity with the target case is greater than the preset threshold is greater than or equal to 1. In this scenario, the search apparatus may select a historical case whose similarity with the target case is greater than the preset threshold and that has a highest priority, as the reference case.

Generally, each case has a corresponding priority. A priority is used to indicate importance of the case. For example, in an electronic medical record, a priority of an electronic medical record in a Grade III Level A hospital is higher than that of an electronic medical record in an ordinary community hospital.

The first characteristic in this embodiment of the present invention is a status of a correspondence between each of the n named entities in the target case and a to-be-analyzed user, and the second characteristic is a corresponding function impact of a preset m, in the n named entities in the target case, on a target named entity. Therefore, the first characteristic and the second characteristic can accurately reflect related information of each named entity in the target case. Correspondingly, the target characteristic vector corresponding to the target case generated based on the first characteristic and the second characteristic can accurately represent key information of the target case. In this way, accuracy in determining a reference case can be improved by using the target characteristic vector corresponding to the target case to search for the reference case.

An embodiment of the present invention provides a search apparatus, and the search apparatus is configured to perform the operations performed by the search apparatus in the search method. The search apparatus provided by this embodiment of present invention may include modules corresponding to corresponding operations.

In this embodiment of the present invention, the search apparatus may be divided into function modules according to the foregoing method example. For example, the function module division may be performed by function, or two or more functions may be integrated into one processing module. The integrated module may be implemented in a form of hardware, or may be implemented in a form of a software function module. The module division in this embodiment of the present invention is schematic and is merely logical function division. There may be another division manner in actual implementation.

Figure 4:
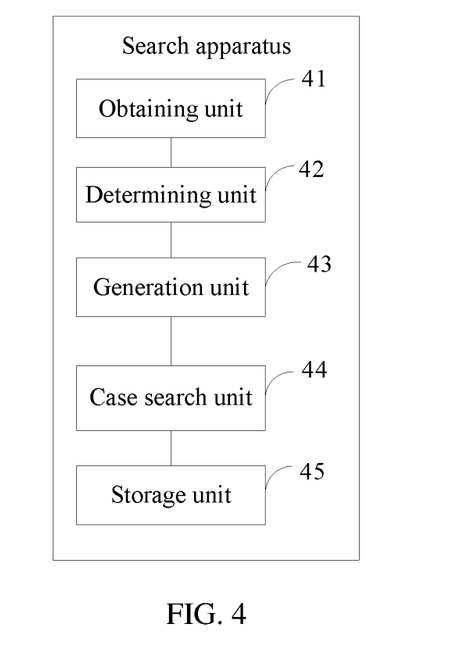
FIG. 4 is a schematic structural diagram 1 of a search apparatus according to an embodiment of the present invention.

If function module division is performed by function, FIG. 4 shows a possible structural diagram of a search apparatus according to the foregoing embodiments. As shown in FIG. 4, the search apparatus includes an obtaining unit 41, a determining unit 42, a generation unit 43, and a case search unit 44. The obtaining unit 41 is configured to support the search apparatus in performing S300 and S303 in FIG. 3; the determining unit 42 is configured to support the search apparatus in performing S301 in FIG. 3; the generation unit 43 is configured to support the search apparatus in performing S302 in FIG. 3; the case search unit 44 is configured to support the search apparatus in performing S304 in FIG. 3. For all the related content of various operations according to the foregoing method embodiment, refer to the function descriptions of corresponding function modules. Details are not described here again. The search apparatus further includes a storage unit 45, and the storage unit 45 is configured to store a database, where the database includes a correspondence between a characteristic of a historical case and a characteristic vector corresponding to the historical case.

Figure 5:
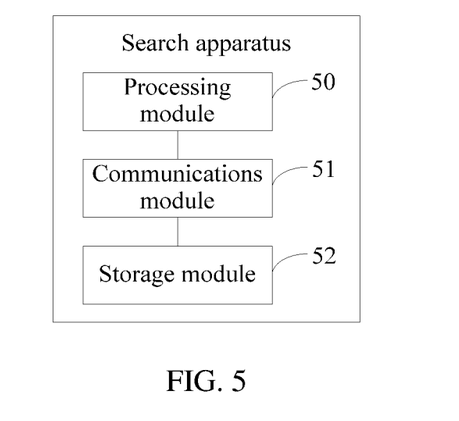
FIG. 5 is a schematic structural diagram 2 of a search apparatus according to an embodiment of the present invention.

If an integrated unit is used, FIG. 5 shows a possible schematic structural diagram of a search apparatus according to the foregoing embodiments. As shown in FIG. 5, the search apparatus includes a processing module 50 and a communications module 51. The processing module 50 is configured to control and manage actions of the search apparatus. For example, the processing module 50 is configured to support the search apparatus in performing S300 to S304 in FIG. 3, and/or is applied to other processes of technologies described herein. The communications module 51 is configured to support the search apparatus in communicating with another communication device. The search apparatus may further include a storage module 52, where the storage module 52 is configured to store a database, and may be further configured to store program code and data of the search apparatus.

The processing module 50 may be a processor or a controller, for example, may be a central processing unit (CPU) or a digital signal processor (The processing module 50 may implement or execute various example logical blocks, modules, and circuits described with reference to content disclosed in the present invention. The communications module 51 may be a transceiver, a transceiver circuit, a communications interface, or the like. The storage module 52 may be a memory.

Figure 6:
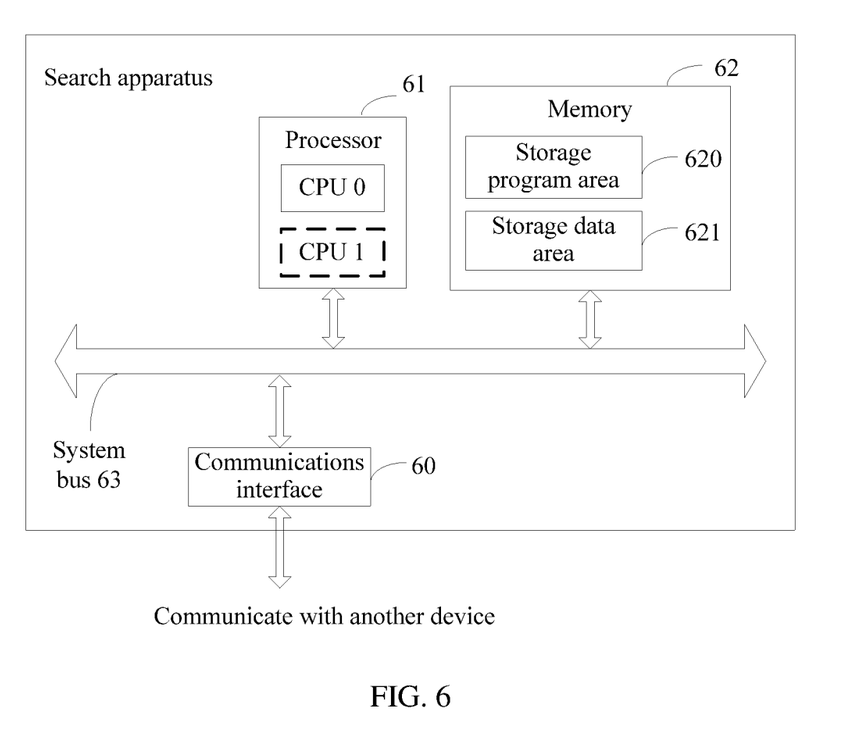
FIG. 6 is a schematic structural diagram 3 of a search apparatus according to an embodiment of the present invention.

When the processing module 50 is a processor, the communications module 51 is a communications interface, and the storage module 52 is a memory, the search apparatus according to this embodiment of the present invention may be a search apparatus shown in FIG. 6.

As shown in FIG. 6, the search apparatus includes a communications interface 60, a processor 61, and a memory 62. The communications interface 60, the processor 61, and the memory 62 are connected by using a system bus 63 to complete communication with each other.

When the search apparatus is operating, the search apparatus performs the search method in the embodiment shown in FIG. 3. For the search method, refer to the related descriptions in the embodiment shown in FIG. 3. Details are not repeated herein.

The communications interface 60 is configured to communicate with another device.

The memory 62 may be configured to store a database, and may be further configured to store a software program and an application module. The processor 61 executes various function applications and data processing of the search apparatus by running the software program and the application module stored in the memory 62.

The memory 62 may mainly include a storage program area 620 and a storage data area 621, where the storage program area 620 may store an operating system, and an application program required by at least one function, such as a function of obtaining a named entity of a case; and the storage data area 621 may store a database.

The memory 62 may be a read-only memory (ROM), or another type of static storage device that may store static information and instructions, or a random access memory (RAM) or another type of dynamic storage device that may store information and instructions, or may be an electrically erasable programmable read-only memory (EEPROM), a disk storage medium or another magnetic storage device, or any other medium that can be used to carry or store desired program code in a form of an instruction or a data structure and that can be accessed by the search apparatus, but is not limited thereto.

The memory 62 may exist independently, and may be connected to the processor 61 by using the bus 63. The memory 62 may alternatively be integrated with the processor 61.

The processor 61 may be a control center of the search apparatus. The processor 61 is connected to various parts of the entire search apparatus by using various interfaces and lines, and executes various functions and data processing of the search apparatus by running or executing the software program and/or the application module stored in the memory 62 and by invoking data stored in the memory 62, so as to provide overall monitoring for the search apparatus.

In an implementation, in an embodiment, the processor 61 may include one or more CPUs. For example, the processor 61 in FIG. 6 includes a CPU0 and a CPU1.

The bus 63 may be divided into an address bus, a data bus, a control bus, and the like. For clear description in this embodiment of the present invention, various buses in FIG. 6 are marked as the system bus 63.

This embodiment of the present invention provides a search apparatus. First, the search apparatus obtains n named entities in a current to-be-analyzed target case, and determines a first characteristic and a second characteristic, where the named entity is an entity identified with a proprietary name in a field to which the target case belongs; the first characteristic is a status of a correspondence between each of the n named entities and a to-be-analyzed user, where the status includes presence or absence; and the second characteristic is a corresponding function impact of a preset m on a target named entity, where the function impact includes facilitation or suppression, and the target named entity belongs to the n named entities. Then, the search apparatus generates, based on the first characteristic and the second characteristic and according to a preset vector generation rule, a target characteristic vector corresponding to the target case. Finally, the search apparatus obtains each historical case in a database and a characteristic vector corresponding to each historical case, separately calculates a similarity between the target characteristic vector and the characteristic vector corresponding to each historical case, and selects a historical case whose similarity result meets a preset condition as a reference case.

The first characteristic in this embodiment of the present invention is a status of a correspondence between each of the n named entities in the target case and a to-be-analyzed user, and the second characteristic is a corresponding function impact of a preset m, in the n named entities in the target case, on a target named entity. Therefore, the first characteristic and the second characteristic can accurately reflect related information of each named entity in the target case. Correspondingly, the target characteristic vector corresponding to the target case generated based on the first characteristic and the second characteristic can accurately represent key information of the target case. In this way, accuracy in determining a reference case can be improved by using the target characteristic vector corresponding to the target case to search for the reference case.

Method or algorithm operations described in combination with the content disclosed in the present invention may be implemented by hardware, or may be implemented by a processor by executing a software instruction. The software instruction may include a corresponding software module. The software module may be stored in a RAM, a flash memory, a ROM, an erasable programmable ROM (EPROM), an electrically erasable programmable ROM (EEPROM), a register, a hard disk, a mobile hard disk, a compact disc read-only memory (CD-ROM), or any other form of storage medium well-known in the art. For example, a storage medium is coupled to a processor, so that the processor can read information from the storage medium or write information into the storage medium. Certainly, the storage medium may be a component of the processor. The processor and the storage medium may be located in the application-specific integrated circuit (ASIC).

The foregoing descriptions about implementations allow a person skilled in the art to understand that, for the purpose of convenient and brief description, division of the foregoing function modules is taken as an example for illustration. In actual application, the foregoing functions can be allocated to different modules and implemented according to a requirement, that is, an inner structure of an apparatus is divided into different function modules to implement all or part of the functions described above. For a detailed working process of the foregoing system, apparatus, and unit, reference may be made to a corresponding process in the foregoing method embodiments, and details are not described herein again.

In the several embodiments provided in this application, it should be understood that the disclosed system, apparatus, and method may be implemented in other manners. For example, the described apparatus embodiment is merely an example. For example, the module or unit division is merely logical function division and may be other division in actual implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected according to actual requirements to achieve the objectives of the solutions of the embodiments.

In addition, functional units in the embodiments of the present invention may be integrated into one processing unit, or each of the units may exist alone physically, or two or more units are integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage medium. Based on such an understanding, the technical solutions of the present invention essentially, or the part contributing to the prior art, or all or some of the technical solutions may be implemented in the form of a software product. The computer software product is stored in a storage medium and includes several instructions for instructing a computer device (which may be a personal computer, a server, or a network device) or a processor to perform all or some of the operations of the methods described in the embodiments of the present invention. The foregoing storage medium includes: any medium that can store program code, such as a flash memory, a removable hard disk, a read-only memory, a random access memory, a magnetic disk, or an optical disc.

The foregoing descriptions are merely specific implementations of the present invention, but are not intended to limit the protection scope of the present invention. Any variation or replacement readily figured out by a person skilled in the art within the technical scope disclosed in the present invention shall fall within the protection scope of the present invention. Therefore, the protection scope of the present invention shall be subject to the protection scope of the claims.

What is claimed is:

1. A search method, comprising:
    obtaining n named entities in a current to-be-analyzed target case, wherein each named entity of the n named entities is identified with a proprietary name in a field to which the current to-be-analyzed target case belongs, and n is a positive integer;
    determining one or more first characteristics and one or more second characteristics, wherein each of the one or more first characteristics indicates a presence or an absence of a correspondence between each of the n named entities and a to-be-analyzed user, and each of the one or more second characteristics indicates a facilitation or a suppression of m named entities on a target named entity of the n named entities, and $m \leq C_n^2$;
    generating, based on the one or more first characteristics and the one or more second characteristics and according to a preset vector generation rule, a target characteristic vector corresponding to the current to-be-analyzed target case, wherein the target characteristic vector includes a plurality of elements, each element representing a numeric value corresponding to one of the one or more first characteristics or one of the one or more second characteristics;
    obtaining each historical case having the n named entities from a database and a characteristic vector corresponding to each historical case; and
    calculating a similarity between the target characteristic vector and the characteristic vector corresponding to each historical case, and selecting a historical case whose similarity result meets a preset condition as a reference case.

2. The search method according to claim 1, wherein the generating of the target characteristic vector corresponding to the target case comprises:
    determining, according to a preset numeralization manner, a numeric value corresponding to each first characteristic and a numeric value corresponding to each second characteristic;
    generating, according to the preset vector generation rule, the numeric value corresponding to the first characteristic, and the numeric value corresponding to the second characteristic, a characteristic vector corresponding to the target case; and performing dimension reduction processing on the characteristic vector corresponding to the target case to generate the target characteristic vector corresponding to the target case.

3. The search method according to claim 1, wherein the search method is applicable to a medical field, and the target case is a current to-be-analyzed electronic medical record; the obtaining of the n named entities in a current to-be-analyzed target case comprises:

obtaining the current to-be-analyzed electronic medical record;

performing word segmentation and stop word deletion processing on the current to-be-analyzed electronic medical record to obtain a word set; and performing medical-field named-entity identification on a word in the word set to determine the n named entities in the current to-be-analyzed electronic medical record.

4. The search method according to claim 1, wherein
the preset condition is that a historical case with a highest similarity to the target case is selected as the reference case, or a historical case whose similarity to the target case is greater than a preset threshold is selected as the reference case.

5. A search apparatus, comprising:
an obtaining unit, configured to obtain n named entities in a current to-be-analyzed target case, wherein each named entity is an entity identified with a proprietary name in a field to which the target case belongs, and n is a positive integer;
a determining unit, configured to determine one or more first characteristics and one or more second characteristics, wherein each of the one or more first characteristics indicates a presence or an absence of a correspondence between each of the n named entities and a to-be-analyzed user, and, each of the one or more second characteristics indicates a facilitation or a suppression of m named entities on a target named entity of the n named entities, and $m \leq C_n^2$;
a generation unit, configured to generate, based on the one or more first characteristics and the one or more second characteristics and according to a preset vector generation rule, a target characteristic vector corresponding to the target case, wherein
the obtaining unit is further configured to obtain each historical case having the n named entities from a database and a characteristic vector corresponding to each historical case; and
a case search unit, configured to calculate a similarity between the target characteristic vector generated by the generation unit and the characteristic vector corresponding to each historical case obtained by the obtaining unit, and select a historical case whose similarity result meets a preset condition as a reference case.

6. The search apparatus according to claim 5, wherein:
the determining unit is further configured to determine, according to a preset numeralization manner, a numeric value corresponding to each first characteristic and a numeric value corresponding to each second characteristic; and
the generation unit is configured to generate, according to the preset vector generation rule, the numeric value corresponding to the first characteristic, and the numeric value corresponding to the second characteristic, a characteristic vector corresponding to the target case, and is configured to perform dimension reduction processing on the characteristic vector corresponding to the target case to generate the target characteristic vector corresponding to the target case.

7. The search apparatus according to claim 5, wherein the search apparatus is applicable to a medical field, and the target case is a current to-be-analyzed electronic medical record; and the obtaining unit is configured to:

obtain the current to-be-analyzed electronic medical record;

perform word segmentation and stop word deletion processing on the current to-be-analyzed electronic medical record to obtain a word set; and perform medical-field named-entity identification on a word in the word set to determine the n named entities in the current to-be-analyzed electronic medical record.

8. The search apparatus according to claim 5, wherein
the preset condition is that a historical case with a highest similarity to the target case is selected as the reference case, or a historical case whose similarity to the target case is greater than a preset threshold is selected as the reference case.

9. A search apparatus, comprising:
a memory;
a processor; and
a communications interface;
wherein the memory, the processor, and the communications interface are connected by using a system bus; and
wherein the memory is configured to store computer instructions, which, when executed by the processor, enable the search apparatus to perform operations comprising:
obtaining n named entities in a current to-be-analyzed target case, wherein each named entity of the n named entities is identified with a proprietary name in a field to which the current to-be-analyzed target case belongs, and n is a positive integer;
determining one or more first characteristics and one or more second characteristics, wherein each of the one or more first characteristics indicates a presence or an absence of a correspondence between each of the n named entities and a to-be-analyzed user, and each of the one or more second characteristics indicates a facilitation or a suppression of m named entities on a target named entity of the n named entities, and $m \leq C_n^2$;
generating, based on the one or more first characteristics and the one or more second characteristics and according to a preset vector generation rule, a target characteristic vector corresponding to the current to-be-analyzed target case, wherein the target characteristic vector includes a plurality of elements, each element representing numeric value corresponding to one of the one or more first characteristics or one of the one or more second characteristics;
obtaining each historical case having the n named entities from a database and a characteristic vector corresponding to each historical case; and
calculating a similarity between the target characteristic vector and the characteristic vector corresponding to each historical case, and selecting a historical case whose similarity result meets a preset condition as a reference case.

10. The search apparatus according to claim 9, the generating of the target characteristic vector corresponding to the target case comprises:

determining, according to a preset numeralization manner, a numeric value corresponding to each first characteristic and a numeric value corresponding to each second characteristic;

generating, according to the preset vector generation rule, the numeric value corresponding to the first characteristic, and the numeric value corresponding to the second characteristic, a characteristic vector corresponding to the target case; and performing dimension reduction processing on the characteristic vector corresponding to the target case to generate the target characteristic vector corresponding to the target case.

11. The search apparatus according to claim 9, wherein the operations are applicable to a medical field, and the target case is a current to-be-analyzed electronic medical record;

the obtaining of the n named entities in a current to-be-analyzed target case comprises:

obtaining the current to-be-analyzed electronic medical record;

performing word segmentation and stop word deletion processing on the current to-be-analyzed electronic medical record to obtain a word set; and performing medical-field named-entity identification on a word in the word set to determine the n named entities in the current to-be-analyzed electronic medical record.

12. The search apparatus according to claim 9, wherein the preset condition is that a historical case with a highest similarity to the target case is selected as the reference case, or a historical case whose similarity to the target case is greater than a preset threshold is selected as the reference case.

* * * * *